(12) United States Patent
Schmidt et al.

(10) Patent No.: US 10,128,525 B2
(45) Date of Patent: Nov. 13, 2018

(54) PREPARATION OF IMIDES CONTAINING A FLUOROSULFONYL GROUP

(71) Applicant: ARKEMA FRANCE, Colombes (FR)

(72) Inventors: Gregory Schmidt, Saint Andeol le Chateau (FR); Sophie Audureau, Feyzin (FR)

(73) Assignee: ARKEMA FRANCE, Colombes (FR)

(*) Notice: Subject to any disclaimer, the term of this patent is extended or adjusted under 35 U.S.C. 154(b) by 108 days.

(21) Appl. No.: 15/304,577

(22) PCT Filed: Apr. 1, 2015

(86) PCT No.: PCT/FR2015/050845
§ 371 (c)(1),
(2) Date: Oct. 17, 2016

(87) PCT Pub. No.: WO2015/158979
PCT Pub. Date: Oct. 22, 2015

(65) Prior Publication Data
US 2017/0047607 A1 Feb. 16, 2017

(30) Foreign Application Priority Data
Apr. 18, 2014 (FR) ..................... 14 53523

(51) Int. Cl.
| | | |
|---|---|---|
| *H01M 4/82* | (2006.01) | |
| *H01M 10/04* | (2006.01) | |
| *C01B 21/086* | (2006.01) | |
| *C07C 303/40* | (2006.01) | |
| *H01M 10/0568* | (2010.01) | |
| *H01M 10/52* | (2006.01) | |
| *H01M 10/0525* | (2010.01) | |

(52) U.S. Cl.
CPC .......... *H01M 10/04* (2013.01); *C01B 21/086* (2013.01); *C07C 303/40* (2013.01); *H01M 10/0525* (2013.01); *H01M 10/0568* (2013.01); *H01M 10/52* (2013.01); *H01M 2300/0025* (2013.01)

(58) Field of Classification Search
CPC ............ H01M 10/04; H01M 10/0525; H01M 10/0568; H01M 10/52; H01M 2300/0025; C01B 21/086; C07C 303/40
See application file for complete search history.

(56) References Cited

U.S. PATENT DOCUMENTS

| | | | |
|---|---|---|---|
| 8,134,027 B2 | 3/2012 | Okumura et al. | |
| 9,394,172 B2* | 7/2016 | Schmidt | ............... C01B 21/086 |
| 9,440,852 B2 | 9/2016 | Schmidt | |
| 2011/0034716 A1 | 2/2011 | Okumura et al. | |
| 2012/0014859 A1* | 1/2012 | Honda | ................ C01B 21/093 423/386 |
| 2012/0020867 A1 | 1/2012 | Morinaka et al. | |
| 2012/0041233 A1* | 2/2012 | Sato | ................... C01B 21/0935 564/154 |
| 2013/0068991 A1 | 3/2013 | Sato | |
| 2014/0075746 A1 | 3/2014 | Schmidt | |
| 2014/0369919 A1 | 12/2014 | Schmidt | |

FOREIGN PATENT DOCUMENTS

| | | |
|---|---|---|
| EP | 1122240 A2 | 8/2001 |
| WO | 2009/123328 A1 | 10/2009 |
| WO | 20100010613 A1 | 1/2010 |
| WO | 2011/149095 A1 | 12/2011 |
| WO | 2012/160280 A2 | 11/2012 |

OTHER PUBLICATIONS

Third Party Observation (PCT Administrative Instructions Part 8) issued on Aug. 9, 2016 in International Patent Application PCT/FR2015/050845 (Arkema France), 8 pages.
International Search Report dated Jul. 13, 2015 issued in corresponding PCT/FR2015/050845 application (3 pages).
M. Beran et al., "A New Method of the Preparation of Imidobis(sulfuric acid) Dihalogenide, (F,Cl), and the Potassium Salt of Imido-bis(sulfuric acid) Difluoride", Z. Anorg. Ailg. Chem., vol. 631, No. 1 (2005) pp. 55-59.
M. Beran et al., "A New Route to the Syntheses of N-(fluorosulfuryl)sulfonamide Salts: Crystal Structure of Ph4P+ [CF3SO2NSO2F]", Polyhedron, vol. 29, No. 3 (2010) pp. 991-994.

* cited by examiner

*Primary Examiner* — Raymond Alejandro
(74) *Attorney, Agent, or Firm* — Buchanan Ingersoll & Rooney P.C.

(57) ABSTRACT

A process for preparing a fluoro compound of formula: $R_2-(SO_2)-NX-(SO_2)-F$ (III) including: (a) a first step for obtaining the chloro compound of formula: $R_1-(SO_2)-NX-(SO_2)-Cl$; (II) this first step including the reaction of the sulfamide of formula: $R_0-(SO_2)-NH_2$ (I) with a sulfureous acid and a chlorinating agent; and (b) a second step for obtaining the fluoro compound of formula (III), this second step including the reaction of the chloro compound of formula (II) with anhydrous hydrofluoric acid in at least one organic solvent; in which: X represents either a hydrogen atom or a monovalent cation M; $R_1$ represents an electron-withdrawing group having a positive Hammett parameter $\sigma_p$; if $R_1$ represents Cl, then $R_0$ represents OH; otherwise, $R_0$ is identical to $R_1$; and if $R_1$ represents Cl, then $R_2$ represents F; otherwise, $R_2$ is identical to $R_1$.

20 Claims, No Drawings

PREPARATION OF IMIDES CONTAINING A FLUOROSULFONYL GROUP

FIELD OF THE INVENTION

The present invention relates to a process for preparing imides containing a fluorosulfonyl group.

TECHNICAL BACKGROUND

By virtue of their very low basicity, anions of sulfonylimide type are increasingly used in the field of energy storage in the form of inorganic salts in batteries, or of organic salts in supercapacitors or in the field of ionic liquids. Since the battery market is in full expansion and reduction of battery manufacturing costs has become a major challenge, an inexpensive large-scale process for synthesizing anions of this type is necessary.

In the specific field of Li-ion batteries, the salt that is currently the most widely used is $LiPF_6$, but this salt has many drawbacks such as limited thermal stability, sensitivity to hydrolysis and thus lower safety of the battery. Recently, novel salts bearing the group $FSO_2^-$ have been studied and have demonstrated many advantages such as better ion conductivity and resistance to hydrolysis. One of these salts, LiFSI ($LiN(FSO_2)_2$) has shown very advantageous properties which make it a good candidate for replacing $LiPF_6$.

Few processes for synthesizing LiFSI or the corresponding acid thereof have been described, but it is clearly seen that, in all these processes, the key step is the step of forming the S—F bond.

A first synthetic route described (Appel & Eisenbauer, Chem. Ber. 95, 246-8, 1962) consists in reacting fluorosulfonic acid ($FSO_3H$) with urea. However, the corrosive and toxic nature of this compound does not allow industrialization of the process.

EP 2 415 709 describes a process based on this route, in which the products of reaction of fluorosulfonic acid with urea are dissolved in water and bis(fluorosulfonyl)imide is precipitated in the form of the salt with tetrabutylammonium. This synthetic route is not viable on a large scale since the overall yield is very low.

Another route consists in reacting difluorosulfoxide with ammonia: see WO 2010/113 835 in this regard. However, this method also forms numerous side products, which necessitates expensive purification steps.

Another route (Ruff & Lustig, Inorg. Synth. 1968, 11, 138-43) consists in synthesizing in a first stage a dichloro compound of formula $(ClSO_2)_2NH$ and then in performing a chlorine/fluorine exchange with $AsF_3$. However, this process is not industrializable due to the high price and the toxicity of $AsF_3$.

WO 02/053 494 describes another route which consists of a Cl/F exchange on $(ClSO_2)_2NH$ using a fluoride of a monovalent cation which may be alkaline or of onium type ($NR_4^+$), in an aprotic solvent. However, according to said document, the reaction is very slow.

Example 10 of WO 2007/068 822 describes the synthesis of bis(fluorosulfonyl)imide in anhydrous hydrofluoric acid (HF). Thus, the reaction is performed in an autoclave with 1 g of bis(chlorosulfonyl)imide and 4 g of anhydrous HF at various reaction temperatures and times. The document teaches that even at temperatures of 130° C., the reaction yield does not exceed 55%. In addition, it teaches that the presence of impurities makes separation difficult at the industrial scale. It concluded that the synthesis of bis(fluorosulfonyl)imide with HF is unsatisfactory, and thus that the use of a lithium fluoride is preferred during the chlorine/fluorine exchange step.

WO 2009/123 328 describes the manufacture of sulfonylimide compounds, via a reaction between amidosulfuric acid and thionyl chloride and then with chlorosulfonic acid, to form bis(chlorosulfonyl)imide, which is then subjected to a fluorination step. The fluorination is performed with a fluoro compound such as $CuF_2$, $ZnF_2$, $SnF_2$, $PbF_2$ or $BiF_3$. However, these fluoro compounds are expensive, making the exploitation of the process at the industrial scale difficult.

There is thus still a need to produce imides containing a sulfonyl group (such as LiFSI), especially via a process that can be performed at the industrial scale.

SUMMARY OF THE INVENTION

The invention relates firstly to a process for preparing a fluoro compound of formula:

$$R_2-(SO_2)-NX-(SO_2)-F \quad (III)$$

comprising:
(a) a first step for obtaining the chloro compound of formula:

$$R_1-(SO_2)-NX-(SO_2)-Cl; \quad (II)$$

this first step comprising the reaction of the sulfamide of formula:

$$R_0-(SO_2)-NH_2 \quad (I)$$

with a sulfureous acid and a chlorinating agent; and
(b) a second step for obtaining the fluoro compound of formula (III), this second step comprising the reaction of the chloro compound of formula (II) with anhydrous hydrofluoric acid in at least one organic solvent;
in which:
X represents either a hydrogen atom or a monovalent cation M;
$R_1$ represents an electron-withdrawing group having a positive Hammett parameter $\sigma_p$;
if $R_1$ represents Cl, then $R_0$ represents OH; otherwise, $R_0$ is identical to $R_1$; and
if $R_1$ represents Cl, then $R_2$ represents F; otherwise, $R_2$ is identical to $R_1$.

According to one embodiment, $R_1$ is chosen from Cl, F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_3HF_6$, $C_4F_9$, $C_4H_2F_7$, $C_4H_4F_5$, $C_5F_{11}$, $C_3F_6OCF_3$, $C_2F_4OCF_3$, $C_2H_2F_2OCF_3$, $CF_2OCF_3$, $C_6F_{13}$, $C_7F_{15}$, $C_8F_{17}$ and $C_9F_{19}$.

According to one embodiment, M represents an alkali metal or alkaline-earth metal cation or a quaternary ammonium cation, and preferably M represents a lithium or sodium cation and more particularly preferably a lithium cation.

According to one embodiment, the sulfureous acid used in the first step is chosen from chlorosulfonic acid, sulfuric acid, oleum and mixtures thereof.

According to one embodiment, the chlorinating agent used in the first step is chosen from thionyl chloride, oxalyl chloride, phosphorus pentachloride, phosphonyl trichloride, phosphoryl trichloride and mixtures thereof.

According to one embodiment:
a catalyst is used for the reaction of the sulfamide with the sulfureous acid and the chlorinating agent in the first step, which is preferably chosen from a tertiary amine such as methylamine, triethylamine or diethylmethylamine, or pyridine and derivatives thereof such as 2,6-lutidine; and/or the reaction of the sulfamide with the sulfureous acid and the chlorinating agent in the first step is performed at a temperature of between 30 and 150° C.; and/or the reaction of the sulfamide with the sulfureous acid and the chlorinating agent in the first step is performed at a pressure of between 1 and 7 bar absolute.

According to one embodiment:

the mole ratio between the sulfureous acid and the sulfamide used in the first step is between 1 and 5; and/or the mole ratio between the chlorinating agent and the sulfamide used in the first step is between 1 and 10.

According to one embodiment, the organic solvent in the second step has a donor number of between 1 and 70 and advantageously between 5 and 65.

According to one embodiment, the organic solvent in the second step is chosen from esters, nitriles, dinitriles, ethers, diethers, amines and phosphines, and mixtures thereof.

According to one embodiment:

the reaction of the chloro compound of formula (II) with anhydrous hydrofluoric acid of the second step is performed at a temperature of between 0° C. and the boiling point of the organic solvent, preferably between 5° C. and the boiling point of the organic solvent; and/or the reaction of the chloro compound of formula (II) with anhydrous hydrofluoric acid of the second step is performed at a pressure of between 0 and 16 bar absolute.

According to one embodiment, the chloro compound of formula (II) is dissolved in the organic solvent prior to the second reaction step.

According to one embodiment:

the mass ratio between the chloro compound of formula (II) and the organic solvent used in the reaction of the chloro compound of formula (II) with anhydrous hydrofluoric acid of the second step is between 0.001 and 10 and preferably between 0.005 and 5; and/or the mole ratio between the chloro compound of formula (II) and hydrofluoric acid used in the reaction of the chloro compound of formula (II) with anhydrous hydrofluoric acid of the second step is between 0.01 and 0.5 and preferably between 0.05 and 0.5.

According to one embodiment, the reaction of the sulfamide with the sulfureous acid and the chlorinating agent of the first step provides the chloro compound of formula:

$$R_1-(SO_2)-NH-(SO_2)-Cl; \quad (IIa)$$

the first step also comprising the reaction of the chloro compound of formula (IIa) with a base, for obtaining the chloro compound of formula:

$$R_1-(SO_2)-NM-(SO_2)-Cl; \quad (IIb)$$

in which M represents a monovalent cation.

According to one embodiment, said base is chosen from alkali metal carbonates, alkaline-earth metal carbonates, alkali metal hydroxides, alkaline-earth metal hydroxides, tertiary amines in a polar organic solvent, and mixtures thereof.

According to one embodiment, the process comprises, after the second step:

(c) a third step of neutralization of the compound of formula (III), preferably by adding a base chosen from alkali metal carbonates, alkaline-earth metal carbonates, alkali metal hydroxides, alkaline-earth metal hydroxides and mixtures thereof.

According to one embodiment, the fluoro compound of formula (III) obtained in the second step is a compound of formula:

$$R_2-(SO_2)-NH-(SO_2)-F \quad (IIIa)$$

and the third step of neutralization allows the compound of formula (IIIa) to be converted into a compound of formula:

$$R_2-(SO_2)-NM\text{-}(SO_2)-F \quad (IIIa)$$

in which M represents a monovalent cation.

According to one embodiment, the process comprises, after the second step or, where appropriate, the third step, a final step of cation exchange, preferably by placing in contact with an alkali metal or alkaline-earth metal or quaternary ammonium fluoride, chloride, carbonate, hydroxide, sulfate, chlorate, perchlorate, nitrite or nitrate.

According to one embodiment, the process makes it possible to obtain $LiN(FSO_2)_2$, $LiN(SO_2CF_3)(SO_2F)$, $LiN(SO_2C_2F_5)(SO_2F)$, $LiN(SO_2CF_2OCF_3)(SO_2F)$, $LiN(SO_2C_3HF_6)(SO_2F)$, $LiN(SO_2C_4F_9)(SO_2F)$, $LiN(SO_2C_5F_{11})(SO_2F)$, $LiN(SO_2C_6F_{13})(SO_2F)$, $LiN(SO_2C_7F_{15})(SO_2F)$, $LiN(SO_2C_8F_{17})(SO_2F)$ or $LiN(SO_2C_9F_{19})(SO_2F)$, and preferably $LiN(FSO_2)_2$.

The invention also relates to a process for manufacturing an electrolyte, comprising the preparation of an imide salt of formula (IIIb) $R_2-(SO_2)-NM\text{-}(SO_2)-F$, in which M represents a monovalent cation and $R_2$ represents an electron-withdrawing group having a positive Hammett parameter $\sigma_p$, via the process described above, and dissolution thereof in a solvent, said imide salt preferably being a lithium or sodium salt.

The invention also relates to a process for manufacturing a battery or a battery cell, comprising the manufacture of an electrolyte according to the above process and the insertion of this electrolyte between an anode and a cathode.

The invention also relates to a composition comprising at least 99.9% by mass of an imide salt of formula:

$$R_2-(SO_2)-NM\text{-}(SO_2)-F \quad (IIIb)$$

in which M represents a monovalent cation and $R_2$ represents an electron-withdrawing group having a positive Hammett parameter $\sigma_p$, the composition comprising a mass content of total fluorides of from 1 to 500 ppm, and/or a mass content of total chlorides of from 1 to 200 ppm.

According to one embodiment, the mass content of total fluorides is from 1 to 250 ppm and/or the mass content of total chlorides is from 1 to 100 ppm.

According to one embodiment, the composition comprises a mass content of nitrates of less than or equal to 250 ppm, preferably less than or equal to 150 ppm; and/or a mass content of sulfates of less than or equal to 250 ppm, preferably less than or equal to 150 ppm.

According to one embodiment:

M represents Li or Na; and/or $R_2$ represents F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_3HF_6$, $C_4F_9$, $C_4H_2F_7$, $C_4H_4F_5$, $C_5F_{11}$, $C_3F_6OCF_3$, $C_2F_4OCF_3$, $C_2H_2F_2OCF_3$, $CF_2OCF_3$, $C_6F_{13}$, $C_7F_{15}$, $C_8F_{17}$ or $C_9F_{19}$, F being preferred.

According to one embodiment, the imide salt is $LiN(FSO_2)_2$, $LiN(SO_2CF_3)(SO_2F)$, $LiN(SO_2C_2F_5)(SO_2F)$, $LiN(SO_2CF_2OCF_3)(SO_2F)$, $LiN(SO_2C_3HF_6)(SO_2F)$, $LiN(SO_2C_4F_9)(SO_2F)$, $LiN(SO_2C_5F_{ii})(SO_2F)$, $LiN(SO_2C_6F_{13})(SO_2F)$, $LiN(SO_2C_7F_{15})(SO_2F)$, $LiN(SO_2C_8F_{17})(SO_2F)$ or $LiN(SO_2C_9F_{19})(SO_2F)$, and preferably $LiN(FSO_2)_2$.

The present invention makes it possible to overcome the drawbacks of the prior art. The invention more particularly provides a process for producing imides containing a sulfonyl group (such as LiFSI) which may be performed at the industrial scale, and without entailing excessive cost.

This is mainly accomplished by means of the fluorination reaction of a bis(sulfonyl)imide chloro compound with anhydrous hydrofluoric acid in an organic solvent. It has been observed, surprisingly, that this fluorination reaction gives a yield of greater than 70%.

Thus, the Applicant has overturned the preconception illustrated in WO 2007/068 822.

DESCRIPTION OF EMBODIMENTS OF THE INVENTION

The invention is now described in greater detail and in a nonlimiting manner in the description that follows.

The invention involves preparing a compound comprising at least one fluorosulfonyl group according to a general scheme in at least two steps:
(a) Preparation of a compound comprising at least one chlorosulfonyl group.
(b) Fluorination of the compound from step (a).
In addition, a third step may optionally be envisaged:
(c) Neutralization of the compound from step (b).
In addition, a fourth step may optionally be envisaged, either after the third step or directly after the second step:
(d) Cation exchange.

Step (a)

In step (a), the sulfamide of formula (I) $R_0$—$(SO_2)$—$NH_2$ is reacted with a sulfureous acid and a chlorinating agent, so as to obtain a chloro compound of formula (II) $R_1$—$(SO_2)$—$NX$—$(SO_2)$—$Cl$.

X represents either a hydrogen atom or a monovalent cation denoted M.

When X represents a hydrogen atom, the above chloro compound is the compound of formula (IIa) $R_1$—$(SO_2)$—$NH$—$(SO_2)$—$Cl$.

When X represents a monovalent cation, the chloro compound is the salt of formula (IIb) $R_1$—$(SO_2)$—$NM$-$(SO_2)$—$Cl$, which may also be written as $R_1$—$(SO_2)$—$N^-$—$(SO_2)$—$Cl$, $M^+$.

As monovalent cation, use may be made of an alkali metal or alkaline-earth metal cation or a quaternary ammonium cation. Sodium and, especially, lithium are preferred.

When the chloro compound (II) obtained on conclusion of the first step is the compound of formula (IIa), the reaction of the sulfamide with the sulfureous acid and the chlorinating agent makes it possible to obtain the chloro compound directly.

When the chloro compound (II) obtained on conclusion of the first step is the compound of formula (IIb), the process is performed in two stages:
in a first stage, reaction of the sulfamide with the sulfureous acid and the chlorinating agent, which makes it possible to obtain the chloro compound of formula (IIa):
in a second stage, conversion of the chloro compound of formula (IIa) into the chloro compound of formula (IIb) by reaction with a base.

In all cases, $R_1$ represents an electron-withdrawing group having a positive Hammett parameter $\sigma_p$.

$R_1$ may especially represent Cl, F or an alkyl or alkoxyalkyl group comprising from 1 to 9 carbon atoms, and totally or partially substituted with fluorine. Examples of such groups are the groups: $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_3HF_6$, $C_4F_9$, $C_4H_2F_7$, $C_4H_4F_5$, $C_5F_{11}$, $C_3F_6OCF_3$, $C_2F_4OCF_3$, $C_2H_2F_2OCF_3$, $CF_2OCF_3$, $C_6F_{13}$, $C_7F_{15}$, $C_8F_{17}$ and $C_9F_{19}$.

When $R_1$ represents Cl, then the starting sulfamide is the amidosulfonic acid of formula (I') OH—$(SO_2)$—$NH_2$ ($R_0$ represents OH).

When $R_1$ represents another group, then the starting sulfamide has the formula (I") $R_1$—$(SO_2)$—$NH_2$ ($R_0$ is identical to $R_1$).

The sulfureous acid used for the reaction may be chlorosulfonic acid $ClSO_3H$, or alternatively sulfuric acid or oleum. Combinations of these reagents may also be used.

The chlorinating agent used for the reaction may be chosen from thionyl chloride $SOCl_2$, oxalyl chloride $(COCl)_2$, phosphorus pentachloride $PCl_5$, phosphonyl trichloride $PCl_3$ and phosphoryl trichloride $POCl_3$. Combinations of these reagents may also be used.

A catalyst may also be used to accelerate the reaction, chosen, for example, from a tertiary amine such as methylamine, triethylamine or diethylmethylamine. Use may also be made of pyridine or a derivative thereof such as 2,6-lutidine. The mole ratio between the sulfureous acid and the sulfamide is advantageously between 1 and 5. The mole ratio between the chlorinating agent and the sulfamide is advantageously between 1 and 10, and more particularly: between 1 and 5 when the sulfureous acid is chlorosulfonic acid; and between 2 and 10 when the sulfureous acid is sulfuric acid or oleum.

The reaction temperature is advantageously between 30 and 150° C. The reaction time is advantageously between 1 hour and 7 days. The reaction may advantageously be performed at a pressure of between 1 bar absolute and 7 bar absolute.

The reaction leads to an evolution of HCl gas and also other gases which may be, for example, depending on the chlorinating agent used, CO, $CO_2$ or $SO_2$.

The possible unreacted reagents or degraded products in solution may be removed via a step of purification by filtration or by recrystallization from an apolar solvent such as pentane, toluene or cyclohexane.

As regards the optional reaction for conversion of the chloro compound of formula (IIa) into the chloro compound (salt) of formula (IIb), the process is performed by reacting the chloro compound of formula (IIa) with a base which may be, for example, an alkali metal or alkaline-earth metal carbonate, an alkali metal or alkaline-earth metal hydroxide or a mixture thereof, or alternatively at least one tertiary amine in an organic solvent of polar type.

As organic solvent of polar type, use may be made especially of acetonitrile, dioxane, tetrahydrofuran, ethyl acetate, butyl acetate and combinations thereof.

This reaction may be performed by dissolving the chloro compound of formula (IIa) in the organic solvent, for example at a concentration of $10^{-3}$ to 10 mol/L. The base may be added in liquid or solid form. The base/chloro compound of formula (IIa) mole ratio may be, for example, 1 when the base is a hydroxide or an amine, or 2 when the base is a carbonate. The reaction temperature may be, for example, between −10° C. and 40° C.

At the end of the reaction, the excess base may be filtered off, and the solution may be evaporated.

Step (b)

In step (b), the chloro compound of formula (IIa) or of formula (IIb) obtained on conclusion of step (a) is fluorinated, so as to obtain the fluoro compound of formula (III) $R_1$—$(SO_2)$—$NX$—$(SO_2)$—$F$. When the fluorination involves a chloro compound of formula (IIa), the fluoro compound obtained is the compound of formula (IIIa) $R_2$—$(SO_2)$—NH—$(SO_2)$—F.

When the fluorination involves a chloro compound of formula (IIb), the fluoro compound obtained is the salt of formula (IIIb) $R_2$—$(SO_2)$—NM-$(SO_2)$—F, which may also be written as $R_2$—$(SO_2)$—$N^-$—$(SO_2)$—F, $M^+$.

When $R_1$ represents Cl, $R_2$ represents F.

In all the other cases, $R_2$ is identical to $R_1$ as defined above.

Preferably, $R_2$ represents F, $CF_3$, $CHF_2$, $CH_2F$ or $CF_2OCF_3$. It is particularly preferred for $R_2$ to represent F.

The fluorination reaction uses anhydrous hydrofluoric acid (HF) in an organic solvent.

The organic solvent preferably has a donor number of between 1 and 70 and advantageously between 5 and 65. The donor number of a solvent represents the value $-\Delta H$, $\Delta H$ being the enthalpy of the interaction between the solvent and antimony pentachloride (according to the method described in *Journal of Solution Chemistry*, vol. 13, No. 9, 1984). Organic solvents that may especially be mentioned include esters, nitriles or dinitriles, ethers or diethers, amines and phosphines. Combinations thereof may also be used as organic solvent.

Methyl acetate, ethyl acetate, butyl acetate, acetonitrile, propionitrile, isobutyronitrile, glutaronitrile, dioxane, tetrahydrofuran, triethylamine, tripropylamine, diethylisopropylamine, pyridine, trimethylphosphine, triethylphosphine, diethylisopropylphosphine and mixtures thereof may especially be suitable for use as organic solvents.

The reaction with anhydrous HF may be performed at a temperature preferably between 0° C., preferably 20° C., and the boiling point of the organic solvent used. Advantageously, this temperature is between 5° C., preferably 25° C., and the boiling point of the organic solvent.

According to the present invention, the step of reaction with anhydrous HF is performed at a pressure that is preferably between 0 and 16 bar absolute.

The chloro compound of formula (II) is preferably dissolved in the organic solvent before the step of reaction with anhydrous HF.

The mass ratio between the chloro compound of formula (II) and the organic solvent is preferably between 0.001 and 10, and advantageously between 0.005 and 5.

HF is introduced into the reaction medium preferably in gaseous form.

The mole ratio between the chloro compound of formula (II) and the HF used is preferably between 0.01 and 0.5, and advantageously between 0.05 and 0.5.

The step of reaction with HF may be performed in a closed medium or in an open medium.

Without wishing to be bound by a theory, the Applicant considers that the use of a donor organic solvent makes it possible to form a solvent-HF complex and thus to enhance the nucleophilicity of the fluorine atom. The use of such a complex allows mild fluorination of the chloro compound of formula (II), thus avoiding spurious cleavage reactions.

The process according to the present invention makes it possible to obtain fluorination yields of between 85% and 100%, which represents a marked increase in comparison with the prior art processes.

The fluorination reaction leads to the formation of HCl, the majority of which may be degassed from the reaction medium (just like the excess HF), for example by sparging with a neutral gas (such as nitrogen, helium or argon).

However, the residual HF and/or HCl may be dissolved in the reaction medium. In the case of HCl, the amounts are very low since, at the working pressure and temperature, HCl is mainly in gas form.

Step (c)

After step (b), the reaction medium is thus preferably neutralized, for example using an aqueous solution of an alkali metal or alkaline-earth metal carbonate $M'CO_3.nH_2O$ or of an alkali metal or alkaline-earth metal hydroxide $M'OH.nH_2O$ preferably to obtain a pH of greater than 4. Use may also be made of mixtures of the above carbonates and/or hydroxides.

In the foregoing, M' denotes a monovalent alkali metal or alkaline-earth metal cation.

The residual HF and/or the residual HCl dissolved in the solvent reacts with the above carbonate or hydroxide, so as to form an alkali metal or alkaline-earth metal fluoride M'F (or a mixture of fluorides M'F), or, respectively, an alkali metal or alkaline-earth metal chloride M'Cl (or a mixture of chlorides M'Cl).

The neutralization reaction may be performed, for example, by adding an aqueous solution of the chosen base. The base/fluoro compound of formula (III) mole ratio may be, for example, from 1 to 5 when the base is a hydroxide, or from 0.5 to 5 or from 2 to 10 when the base is a carbonate. The reaction temperature may be, for example, between −10° C. and 40° C.

At the end of the reaction, the excess base may be filtered off, and the solution may be evaporated. This also allows removal of the majority of the fluorides and chlorides formed.

The solution may then be extracted with an organic solvent, which may be, for example, dichloromethane, acetonitrile, ethyl acetate, butyl acetate, diethyl ether, tetrahydrofuran, toluene or a mixture thereof. This extraction may be performed several times to maximize the recovery yield.

The organic phase obtained may then be extracted several times with water to purify the product. The organic solution may then be evaporated to give the desired imide salt containing a fluorosulfonyl group.

The imide salt thus obtained preferably has a mass content of fluorides of less than 500 ppm and more particularly preferably less than 250 ppm.

The imide salt thus obtained also preferably has a mass content of chlorides of less than 200 ppm and more particularly preferably less than 100 ppm.

It should be noted that, in the particular case in which the fluoro compound of formula (IIIa) $R_2$—$(SO_2)$—NH—$(SO_2)$—F is obtained on conclusion of the second step, the third step of neutralization as described above also leads toward converting this compound into the fluoro compound (salt) of formula (IIIb) $R_2$—$(SO_2)$—NM-$(SO_2)$—F, M being equal to M'.

Step (d)

Optionally, a step of cation exchange may be envisaged at the end of the process. This step makes it possible to convert a fluoro compound of formula (IIIb) $R_2$—$(SO_2)$—NM-$(SO_2)$—F into a fluoro compound of formula (IIIc) $R_2$—$(SO_2)$—NM"-$(SO_2)$—F, in which M" represents a cation.

M" may especially represent an alkali metal or alkaline-earth metal cation or a quaternary ammonium cation. It may be, for example, the lithium or sodium cation, more particularly the lithium cation.

This step of cation exchange is performed by placing the fluoro compound of formula (IIIb) in contact with a salt of the cation M", which may be a fluoride, chloride, carbonate, hydroxide, sulfate, chlorate, perchlorate, nitrite or nitrate salt. A combination of these compounds may also be used.

The reaction may be performed, for example, in water or in a polar organic solvent especially such as acetonitrile, N-methylpyrrolidone, dimethylformamide, dimethyl sulfoxide, nitromethane, dioxane, tetrahydrofuran, ethyl acetate, butyl acetate and mixtures thereof.

The reaction may be performed, for example, at a temperature of between 0° and the boiling point of the solvent used.

The reaction time may be, for example, between 1 hour and 5 days.

The mole ratio between the salt of the cation M" and the imide salt may be, for example, between 0.9 and 5. The concentration of imide salt in water or the organic solvent may be, for example, between 0.001 and 5 mol/L.

In the particular case in which the solvent used is water, the reaction medium may then be extracted with an organic solvent which may especially be dichloromethane, acetonitrile, ethyl acetate, butyl acetate, diethyl ether, tetrahydrofuran, toluene or mixtures thereof. This extraction may be performed several times to maximize the recovery yield. The organic phase is then evaporated to obtain the imide salt of formula (IIIc).

The process according to the present invention is particularly advantageous for manufacturing the following imide salts: $LiN(SO_2F)_2$, $LiNSO_2CF_3SO_2F$, $LiNSO_2C_2F_5SO_2F$, $LiNSO_2CF_2OCF_3SO_2F$, $LiNSO_2C_3HF_6SO_2F$, $LiNSO_2C_4F_9SO_2F$, $LiNSO_2C_5F_{11}SO_2F$, $LiNSO_2C_6F_{13}SO_2F$, $LiNSO_2C_7F_{15}SO_2F$, $LiNSO_2C_8F_{17}SO_2F$ and $LiNSO_2C_9F_{19}SO_2F$.

Preferably, these salts are obtained in a purity at least equal to 99.5% by weight, advantageously at least equal to 99.9% by weight. The impurities such as LiCl, LiF or NaCl, NaF and $FSO_3Na$ that may be present in the imide salt each preferably represent less than 1000 ppm, advantageously less than 500 ppm.

The impurity $FSO_3Li$ may be present in a concentration of less than 50 ppm, preferably less than 5 ppm.

The nitrates and sulfates that may be present in the imide salt are advantageously, respectively, present in a mass concentration of less than 250 ppm and preferably less than 150 ppm.

As indicated previously, the content of fluorides that may be present is preferably less than 500 ppm, and more particularly preferably less than 250 ppm.

As indicated previously, the content of chlorides that may be present is preferably less than 200 ppm, and more particularly preferably less than 100 ppm.

These concentrations of impurities are mass concentrations relative to the mass of the desired imide salt.

The imide salt obtained is preferably essentially free of water and of impurities constituted by salts formed from a cation derived from groups 11 to 15 and periods 4 to 6 of the Periodic Table (for example Zn, Cu, Sn, Pb, Bi).

These impurities are harmful to the performance of Li-ion or Na-ion batteries on account of their electrochemical activity.

Preparation of an Electrolyte

The imide salt prepared as described above may be used for the preparation of an electrolyte, by dissolving it in a suitable solvent.

For example, as described in the document *J. Electrochemical Society*, 2011, 158, A74-82, LiFSI may be dissolved to a concentration of 1 mol/L in a mixture of ethylene carbonate (EC), dimethyl carbonate (DMC) and ethyl methyl carbonate (EMC) at 5 to 2 to 3 by volume; such an electrolyte shows very good conductivity, good cycling stability and corrosion of aluminum above 4.2 V.

This electrolyte may then be used for the manufacture of batteries or battery cells, by placing it between a cathode and an anode, in a manner known per se.

EXAMPLES

The examples that follow illustrate the invention without limiting it.

Example 1

Sulfamic acid (1 eq., 0.515 mol, 50 g) is placed in a round-bottomed flask with thionyl chloride (3.75 eq., 1.93 mol, 229.8 g) and 95% sulfuric acid (1 eq., 0.515 mol, 53.1 g) is added at room temperature. The mixture is maintained at the reflux point of the thionyl chloride for 24 hours with stirring. The dichloro compound finally obtained is pale yellow in appearance, with residual undissolved sulfamic acid. The mixture is filtered to remove the sulfamic acid (23.6 g) and the thionyl chloride is then evaporated off under vacuum.

Example 2

1 eq. of sulfamic acid (0.25 mol, 24.25 g) is placed in a glass round-bottomed flask or reactor, followed by thionyl chloride (2.75 eq., 0.69 mol, 81.9 g). Next, chlorosulfonic acid (2 eq., 0.5 mol, 58.25 g) is added very slowly with stirring at room temperature. The mixture is brought gradually to the reflux point of the thionyl chloride (oil bath at 90° C.) and is left at reflux for 24 hours, with continued stirring. Evolution of gas is observed, this gas being trapped in water at the reactor outlet. The product finally recovered in the round-bottomed flask is liquid, slightly orange and highly fuming.

Example 3

28 g of $(ClSO_2)_2NH$ are dissolved in 50 mL of acetonitrile in an 800 mL autoclave. 10 g of HF are then added. The pressure is then 0.34 bar absolute and the temperature is maintained at 10° C. The reaction is left stirring in a closed medium for 18 hours. The excess HF is removed by flushing with an inert gas. The reaction medium is then treated with lithium carbonate. The solution is filtered and then evaporated and the residue is analyzed by $^{19}F$ NMR. The analysis shows the presence of 85% of totally fluorinated product $(FSO_2)_2NLi$, 7.5% of $FSO_3Li$ and 7.5% of $FSO_2NH_2$. These last two products are the compounds formed during the degradation of the starting material.

Example 4

31.7 g of $(ClSO_2)_2NH$ are dissolved in 50 mL of acetonitrile in an 800 mL autoclave. 10 g of HF are then added. The pressure is then 0.75 bar absolute and the temperature is maintained at 20° C. The reaction is left stirring in a closed medium for 18 hours. The excess HF is removed by pumping. The reaction medium is then treated with lithium carbonate. The solution is filtered and then evaporated and the residue is analyzed by $^{19}F$ NMR. The analysis shows the presence of 100% of totally fluorinated product $(FSO_2)_2NLi$ and the absence of the degradation products $FSO_3Li$ and $FSO_2NH_2$.

Example 5

61 g of $(ClSO_2)_2NH$ are dissolved in 50 mL of 1,4-dioxane in an 800 mL autoclave. 20 g of HF are then added. The pressure is then 2.3 bar absolute and the temperature is maintained at 25° C. The reaction is left stirring in a closed medium for 18 hours. The excess HF is removed by pumping. The reaction medium is then treated with lithium carbonate. The solution is filtered and then evaporated and the residue is analyzed by $^{19}F$ NMR. The analysis shows the presence of 100% of totally fluorinated product $(FSO_2)_2NLi$ and the absence of the degradation products $FSO_3Li$ and $FSO_2NH_2$.

Example 6

65 g of $(ClSO_2)_2NH$ are dissolved in 50 mL of 1,4-dioxane in an 800 mL autoclave. 20 g of HF are then added. The pressure is then 0 bar absolute and the temperature is maintained at 25° C. The reaction is left stirring in an open medium for 3 hours. The excess HF is removed by flushing with an inert gas. The reaction medium is then treated with lithium carbonate. The solution is filtered and then evaporated and the residue is analyzed by $^{19}F$ NMR. The analysis shows the presence of 100% of totally fluorinated product $(FSO_2)_2NLi$ and the absence of the degradation products $FSO_3Li$ and $FSO_2NH_2$.

The invention claimed is:

1. A process for preparing a fluoro compound of formula:

$$R_2-(SO_2)-NX-(SO_2)-F \quad (III)$$

comprising:
(a) a first step for obtaining the chloro compound of formula:

$$R_1-(SO_2)-NX-(SO_2)-Cl; \quad (II)$$

this first step comprising the reaction of the sulfamide of formula:

$$R_0-(SO_2)-NH_2 \quad (I)$$

with a sulfureous acid and a chlorinating agent; and
(b) a second step for obtaining the fluoro compound of formula (III), this second step comprising the reaction of the chloro compound of formula (II) with anhydrous hydrofluoric acid in at least one organic solvent;
in which:
X represents either a hydrogen atom or a monovalent cation M;
$R_1$ represents an electron-withdrawing group having a positive Hammett parameter $\sigma_p$;
if $R_1$ represents Cl, then $R_0$ represents OH; otherwise, $R_0$ is identical to $R_1$; and
if $R_1$ represents Cl, then $R_2$ represents F; otherwise, $R_2$ is identical to $R_1$.

2. The process as claimed in claim 1, in which $R_1$ is chosen from Cl, F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_3HF_6$, $C_4F_9$, $C_4H_2F_7$, $C_4H_4F_5$, $C_5F_{11}$, $C_3F_6OCF_3$, $C_2F_4OCF_3$, $C_2H_2F_2OCF_3$, $CF_2OCF_3$, $C_6F_{13}$, $C_7F_{15}$, $C_8F_{17}$ and $C_9F_{19}$.

3. The process as claimed in claim 1, in which M represents an alkali metal or alkaline-earth metal cation or a quaternary ammonium cation.

4. The process as claimed in claim 1, in which the sulfureous acid used in the first step is chosen from chlorosulfonic acid, sulfuric acid, oleum and mixtures thereof.

5. The process as claimed in claim 1, in which the chlorinating agent used in the first step is chosen from thionyl chloride, oxalyl chloride, phosphorus pentachloride, phosphonyl trichloride, phosphoryl trichloride and mixtures thereof.

6. The process as claimed in claim 1, in which:
a catalyst is used for the reaction of the sulfamide with the sulfureous acid and the chlorinating agent in the first step; and/or
the reaction of the sulfamide with the sulfureous acid and the chlorinating agent in the first step is performed at a temperature of between 30 and 150° C.; and/or
the reaction of the sulfamide with the sulfureous acid and the chlorinating agent in the first step is performed at a pressure of between 1 and 7 bar absolute.

7. The process as claimed in claim 1, in which:
the mole ratio between the sulfureous acid and the sulfamide used in the first step is between 1 and 5; and/or
the mole ratio between the chlorinating agent and the sulfamide used in the first step is between 1 and 10.

8. The process as claimed in claim 1, in which the organic solvent in the second step has a donor number of between 1 and 70.

9. The process as claimed in claim 1, in which the organic solvent in the second step is chosen from esters, nitriles, dinitriles, ethers, diethers, amines and phosphines, and mixtures thereof.

10. The process as claimed in claim 1, in which:
the reaction of the chloro compound of formula (II) with anhydrous hydrofluoric acid of the second step is performed at a temperature of between 0° C. and the boiling point of the organic solvent, preferably between 5° C. and the boiling point of the organic solvent; and/or
the reaction of the chloro compound of formula (II) with anhydrous hydrofluoric acid of the second step is performed at a pressure of between 0 and 16 bar absolute.

11. The process as claimed in claim 1, in which the chloro compound of formula (II) is dissolved in the organic solvent prior to the second reaction step.

12. The process as claimed in claim 1, in which:
the mass ratio between the chloro compound of formula (II) and the organic solvent used in the reaction of the chloro compound of formula (II) with anhydrous hydrofluoric acid of the second step is between 0.001 and 10; and/or
the mole ratio between the chloro compound of formula (II) and hydrofluoric acid used in the reaction of the chloro compound of formula (II) with anhydrous hydrofluoric acid of the second step is between 0.01 and 0.5.

13. The process as claimed in claim 1, in which the reaction of the sulfamide with the sulfureous acid and the chlorinating agent of the first step provides the chloro compound of formula:

$$R_1-(SO_2)-NH-(SO_2)-Cl; \quad (IIa)$$

the first step also comprising the reaction of the chloro compound of formula (IIa) with a base, for obtaining the chloro compound of formula:

$$R_1-(SO_2)-NM-(SO_2)-Cl \quad (IIb)$$

in which M represents a monovalent cation.

14. The process as claimed in claim 13, in which said base is chosen from alkali metal carbonates, alkaline-earth metal carbonates, alkali metal hydroxides, alkaline-earth metal hydroxides, tertiary amines in a polar organic solvent, and mixtures thereof.

15. The process as claimed in claim 1, comprising, after the second step:
(c) a third step of neutralization of the compound of formula (III).

16. The process as claimed in claim 15, in which the fluoro compound of formula (III) obtained in the second step is a compound of formula:

$$R_2\text{—}(SO_2)\text{—}NH\text{—}(SO_2)\text{—}F \qquad \text{(IIIa)}$$

and in which the third step of neutralization allows the compound of formula (111a) to be converted into a compound of formula:

$$R_2\text{—}(SO_2)\text{—}NM\text{-}(SO_2)\text{—}F \qquad \text{(IIIb)}$$

in which M represents a monovalent cation.

17. The process as claimed in claim 1, comprising, after the second step or, where appropriate, the third step, a final step of cation exchange.

18. The process as claimed in claim 1, for obtaining $LiN(SO_2F)_2$, $LiN(SO_2CF_3)(SO_2F)$, $LiN(SO_2C_2F_5)(SO_2F)$, $LiN(SO_2CF_2OCF_3)(SO_2F)$, $LiN(SO_2C_3HF_6)(SO_2F)$, $LiN(SO_2C_4F_9)(SO_2F)$, $LiN(SO_2C_5F_{11})(SO_2F)$, $LiN(SO_2C_6F_{13})(SO_2F)$, $LiN(SO_2C_7F_{15})(SO_2F)$, $LiN(SO_2C_8F_{17})(SO_2F)$ or $LiN(SO_2C_9F_{19})(SO_2F)$.

19. A process for manufacturing an electrolyte, comprising the preparation of an imide salt of formula (IIIb) $R_2\text{—}(SO_2)\text{—}NM\text{-}(SO_2)\text{—}F$, in which M represents a monovalent cation and $R_2$ represents an electron-withdrawing group having a positive Hammett parameter $\sigma_p$, via the process of claim 1, and dissolution thereof in a solvent, said imide salt preferably being a lithium, sodium or potassium salt.

20. A process for manufacturing a battery or a battery cell, comprising the manufacture of an electrolyte as claimed in claim 19 and the insertion of this electrolyte between an anode and a cathode.

* * * * *